United States Patent [19]

Zeeh et al.

[11] 4,436,548
[45] Mar. 13, 1984

[54] PLANT GROWTH REGULATING α-AZOLYLGLYCOLS

[75] Inventors: Bernd Zeeh, Ludwigshafen; Norbert Göetz, Worms; Eberhard Ammermann, Ludwigshafen; Johann Jung, Limburgerhof, all of Fed. Rep. of Germany

[73] Assignee: BASF Aktiengesellschaft, Fed. Rep. of Germany

[21] Appl. No.: 324,276

[22] Filed: Nov. 23, 1981

[30] Foreign Application Priority Data

Dec. 18, 1980 [DE] Fed. Rep. of Germany ....... 3047726

[51] Int. Cl.³ .................. A01N 43/50; A01N 43/64; C07D 249/08; C07D 233/60
[52] U.S. Cl. ........................................ 71/76; 71/78; 71/92; 548/101; 548/262; 548/341
[58] Field of Search ............... 548/101, 262, 341; 71/76, 78, 92

[56] References Cited

U.S. PATENT DOCUMENTS 3,952,002  4/1976  Kramer et al. ............. 548/262
4,005,083  1/1977  Buchel et al. ............. 424/269
4,269,845  5/1981  Worthington et al. ......... 548/101

FOREIGN PATENT DOCUMENTS 21345    7/1981  European Pat. Off. ..
2325156  5/1973  Fed. Rep. of Germany .
2324424  5/1973  Fed. Rep. of Germany .
2650831  5/1978  Fed. Rep. of Germany .

OTHER PUBLICATIONS

J. Biol. Chem. 235, No. 2, (1960), p. 475–479.

Primary Examiner—Alton D. Rollins
Attorney, Agent, or Firm—Keil & Witherspoon

[57] ABSTRACT

α-Azolylglycols of the formula

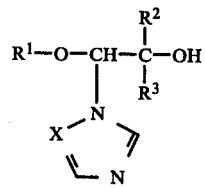

where $R^1$ is alkyl, $R^2$ is alkyl or unsubstituted or substituted phenyl or biphenyl, $R^3$ is hydrogen, alkyl, alkenyl, alkynyl or unsubstituted or substituted benzyl and X is CH or N, their plant-tolerated salts and metal complexes, their preparation, and their use as plant growth regulators.

1 Claim, No Drawings

PLANT GROWTH REGULATING α-AZOLYLGLYCOLS

The present invention relates to novel α-azolyl-glycols, processes for their preparation, agents which contain these compounds and are used for regulating plant growth, and processes for regulating plant growth with these compounds.

The use of 2-chloroethyl-trimethylammonium chloride (chlorocholine chloride, CCC) for influencing plant growth has been disclosed (J. Biol. Chem., 235 (1960), 475). With the aid of this compound, it is possible, for example, to inhibit longitudinal growth in some varieties of cereal, and vegetative growth in some other crops. However, the action of this substance is not always adequate, especially when low amounts are applied, and does not meet practical requirements.

The use of 1-(4'-bromophenyl)-1-allyloxy-2-(1",2",4"-triazol-1"-yl)-ethane for regulating plant growth in rapeseed, wheat, oats, rye and barley has also been disclosed (German Laid-Open Application DOS No. 2,650,831). However, the action of this compound is not always satisfactory, especially when low amounts are applied.

We have found that α-azolylglycols of the formula I

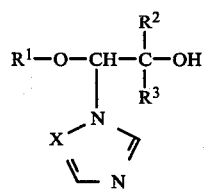

where $R^1$ is alkyl, $R^2$ is alkyl or unsubstituted or substituted phenyl or biphenyl, $R^3$ is hydrogen, alkyl, alkenyl, alkynyl or unsubstituted or substituted benzyl and X is CH or N, and their salts and metal salt complexes, are very useful for influencing plant growth and very well tolerated by plants.

In formula I, $R^1$ is preferably branched or straight-chain alkyl of 1 to 4 C atoms, for example methyl, ethyl, n-propyl, iso-propyl, n-butyl, iso-butyl or tert.-butyl.

$R^2$ is preferably straight-chain alkyl of 1 to 6 carbon atoms, for example methyl, ethyl, propyl, butyl or pentyl, or branched alkyl of 3 to 6 carbon atoms, for example isopropyl, tert.-butyl or 3-methyl-but-1-yl. $R^2$ can also be phenyl or biphenyl which is unsubstituted or mono- or di-substituted by halogen, preferably chlorine or bromine.

$R^3$ is preferably hydrogen, straight-chain alkyl of 1 to 6 carbon atoms, for example methyl, ethyl, propyl, butyl or pentyl, branched alkyl of 3 to 6 carbon atoms, for example iso-propyl or iso-butyl, alkenyl or alkynyl of 2 to 6 carbon atoms, for example vinyl, ethynyl, prop-2-en-1-yl, prop-2-yn-1-yl or 3-methyl-but-2-en-1-yl, or benzyl which is unsubstituted or mono- or di-substituted by halogen, for example fluorine or chlorine.

The novel α-azolylglycols have a center of asymmetry at the acetal carbon atom and, if $R^2$ and $R^3$ are different, also at the carbinol carbon atom. Further centers of asymmetry may also be present, depending on the nature of $R^1$. The compounds can be obtained in the form of pure enantiomers or diastereomers by conventional separation methods. Either the pure enantiomers or diastereomers or the mixtures usually obtained in the synthesis can be used in practice, the latter being preferred.

We have also found that the novel α-azolyl-glycols of the formula I can be prepared by (a) reducing a ketone of the formula II

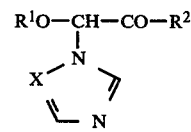

where $R^1$, $R^2$ and X have the above meanings, catalytically or with a complex hydride in the presence of a solvent and in the presence or absence of a reaction accelerator, at from 0° to 100° C., or (b) reacting a ketone of the formula II with a Grignard reagent of the formula IV $$R^3MgHal \qquad IV$$

where $R^3$ has the above meanings and Hal is chlorine, bromine or iodine, in the presence of an inert solvent, at from 0° to 80° C., or (c) reacting an acetal of the formula V

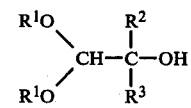

where $R^1$, $R^2$ and $R^3$ have the above meanings, with an inorganic or organic acid chloride and then reacting the product with an azole (triazole or imidazole), in the presence or absence of a solvent and of a base, at from 0° to 100° C.

The starting compounds II can be prepared by reacting an α-halogenoether of the formula III

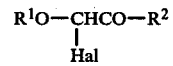

where $R^1$ and $R^2$ have the above meanings and Hal is chlorine or bromine, with an azole (triazole or imidazole) or alkali metal or alkaline earth metal salt thereof, in the presence or absence of a solvent and of a base, at from 0° to 100° C.

The α-halogenoethers of the formula III can be prepared in a conventional manner (cf. German Laid-Open Application DOS No. 2,201,063, B. Mylo, Chem. Ber. 44 (1911), 3212, and Straus and Weber, Ann. 498 (1932) 124). They can also be prepared by halogenating α-alkoxyketones (for example with N-bromosuccinimide).

Some of the alcohols of the formula V are known, for example 1,1-dimethoxy-2-methyl-but-3-yn-2-ol (German Pat. No. 1,768,877) or 1,1-dimethoxy-2-methyl-but-3-en-2-ol (German Pat. No. 1,115,238). However, they can also be prepared by conventional methods, by hydrogenating a ketone of the formula VI $$(R^1O)_2CH-CO-R^2 \qquad VI$$

catalytically or with a complex hydride or by reacting such a ketone with a Grignard reagent of the formula IV.

Suitable inorganic or organic acid halides for process (c) are, for example, thionyl chloride, acetyl chloride and acetyl bromide. Furthermore, all the conventional readily accessible acid halides can be used.

Suitable inorganic or organic bases, which may also be used as acid acceptors in processes a and c, are, for example, alkali metal and alkaline earth metal hydroxides, such as sodium hydroxide, potassium hydroxide and calcium hydroxide, alkali metal carbonates, such as sodium carbonate and potassium carbonate, alkali metal hydrides, such as sodium hydride, alkali metal or alkaline earth metal alcoholates, such as sodium methylate, magnesium methylate and sodium isopropylate, and tertiary amines, such as trimethylamine, triethylamine, N,N-dimethylaniline, N,N-dimethylcyclohexylamine, N-methylpiperidine and pyridine.

The azoles (triazole and imidazole) themselves can also be used as bases. If suitable bases are used, for example alkali metal hydrides, such as sodium hydride, lithium-alkyls, such as butyl-lithium, and alkali metal or alkaline earth metal alcoholates, such as sodium methylate, it is also possible first to convert the azoles into their salts in a prior reaction and then to react the salts.

Preferred solvents or diluents include halohydrocarbons, such as methylene chloride, chloroform, 1,2-dichloroethane and chlorobenzene, aliphatic or aromatic hydrocarbons, such as cyclohexane, petroleum ether, benzene, toluene and the xylenes, esters, such as ethyl acetate, amides, such as dimethylformamide, nitriles, such as acetonitrile, sulfoxides, such as dimethylsulfoxide, ketones, such as acetone and methyl ethyl ketone, and ethers, such as diethyl ether, tetrahydrofuran and dioxane, and appropriate mixtures thereof.

Preferred reaction accelerators are metal halides, such as potassium iodide, crown ethers, quaternary ammonium compounds, such as tetrabutylammonium iodide, and acids, and combinations of these reaction accelerators.

The reactions according to the invention are generally carried out by a continuous or batchwise procedure at from 0° to 150° C. under atmospheric or superatmospheric pressure over a period of from 1 to 60 hours.

The compounds according to the invention are isolated in a conventional manner. In general, the products obtained require no further purification, but they can also be further purified in a conventional manner, for example by recrystallization, extraction, distillation or chromatography.

If desired, the α-azolylglycols of the formula I are then converted to their plant-tolerated salts or to their metal complexes in a conventional manner.

Acids which can be used for salt formation are, for example, hydrochloric acid, hydrobromic acid, sulfuric acid, nitric acid, phosphoric acid, acetic acid and dodecylbenzenesulfonic acid. The effectiveness of the salt depends on the cation, so that any desired anion may be chosen.

Metal complexes are formed by adding the new compounds onto the cations of metal salts. Particularly suitable salts are copper-II chloride, copper-II sulfate, copper-II nitrate, zinc-II chloride, iron-III chloride, manganese-II chloride and nickel-II bromide.

The following Examples illustrate the preparation of the novel substances:

EXAMPLE 1

(a) Preparation of the starting material:

36.8 g of acetyl bromide are added dropwise to 48 g of 1,1-dimethoxy-3,3-dimethylbutan-2-one (cf. J. B. Wright J. Am. Chem. Soc. 77 (1955), 4883), with stirring. During this addition, the temperature rises to 53° C. After this solution has been stirred for one hour, it is added dropwise to a solution of 41.4 g of triazole in 100 ml of dimethylformamide and 100 ml of tetrahydrofuran. The reaction mixture is stirred for three hours and then concentrated, the residue is taken up in methylene chloride and the mixture is washed three times with 50 ml of water each time. The organic phase is separated off, dried and concentrated. The oil which remains is distilled in a column. 44 g of 1-(1',2',4'-triazol-1'-yl)-1p-methoxy-3,3-dimethyl-butan-2-one pass over at from 84° to 86° C./0.1 mbar.

(b) Preparation of the end product:

4.5 g of sodium borohydride are added a little at a time to 39.4 g of 1-(1',2',4'-triazol-1'-yl)-1-methoxy-3,3-dimethylbutan-2-one in 80 ml of methanol at from 10° to 20° C. The reaction mixture is then refluxed for 1 hour and is stirred into 80 ml of water and extracted three times with 100 ml of methylene chloride each time. The organic phase is separated off, dried and concentrated. The oil which remains crystallizes out from petroleum ether. 34 g of 1-(1',2',4'-triazol-1'-yl)-1-methoxy-3,3-dimethylbutan-2-ol of melting point 62°–64° C. are thus obtained.

Calculated: C: 54.3; H: 8.6; N: 21.1. Found: C: 54.5; H: 8.4; N: 21.1.

EXAMPLE 2

A solution of 1-(1',2',4'-triazol-1'-yl)-1-methoxyacetone in 100 ml of ether is added dropwise to a solution of 0.2 mole of 4-chlorophenylmagnesium bromide (prepared from 4.9 g of magnesium and 38.3 g of 4-bromochlorobenzene) in 150 ml of ether. The reaction mixture is then refluxed for 5 hours. 50 g of ice are added to the cooled reaction mixture, and 25% strength aqueous ammonium chloride solution is then introduced dropwise until the phases separate cleanly. The organic phase is separated off and the aqueous phase is extracted twice with 100 ml of ether each time. The combined ether phases are washed neutral with water, and are dried and concentrated. 23 g of crystalline 1-(1',2',4'-triazol-1'-yl)-1-methoxy-2-(4'-chlorophenyl)-propan-2-ol of melting point 80°–82° C. are obtained from petroleum ether.

EXAMPLE 3

12.3 g of acetyl bromide are added dropwise to 14.8 g of 1,1-(dimethoxy)-2-methyl-butan-2-ol, with stirring. During this addition, the temperature rises to 60° C. After this reaction mixture has been stirred for one hour, it is added dropwise to a solution of 13.8 g of triazole in 100 ml of tetrahydrofuran and 50 ml of dimethylformamide. After the reaction mixture has been stirred overnight, it is concentrated, the residue is taken up in methylene chloride and the methylene chloride mixture is washed three times with 50 ml of water each time. The organic phase is dried and concentrated. The oil which remains is distilled. 6 g of 1-(1',2',4'-triazol-1'-yl)-1-methoxy-2-methylbutan-2-ol pass over at from 95° to 110° C./0.4 mbar.

The following α-azolylglycols of the formula I can be prepared by a method similar to that of Examples 1–3:

| No. | R¹ | R² | R³ | X | Physical data |
|---|---|---|---|---|---|
| 4 | CH₃ | 2,4-Cl₂—C₆H₃— | H | N | m.p. 136–138° C. |
| 5 | C₂H₅ | 2,4-Cl₂—C₆H₃— | H | N | m.p. 113–115° C. |
| 6 | CH₃ | C₆H₅— | CH₃ | N | m.p. 102–104° C. |
| 7 | n-C₄H₉ | 4-Cl—C₆H₄— | CH₃ | N | m.p. 58–70° C. |
| 8 | iso-C₄H₉ | 4-Cl—C₆H₄— | CH₃ | N | oil |
| 9 | CH₃ | 4-(C₆H₅)—C₆H₄— | CH₃ | N | m.p. 176–178° C. |
| 10 | CH₃ | 4-Cl—C₆H₄—CH₂— | CH₃ | N | m.p. 110–112° C. |
| 11 | CH₃ | 2,4-Cl₂—C₆H₃— | CH₃ | N | m.p. 135–137° C. |
| 12 | C₂H₅ | 2,4-Cl₂—C₆H₃— | CH₃ | N | m.p. 150–152° C. |
| 13 | CH₃ | CH₃ | H | N | m.p. 140–142° C. |
| 14 | CH₃ | CH₃ | H | CH | |
| 15 | CH₃ | tert-C₄H₉— | CH₃ | N | m.p. 85–86° C. |
| 16 | CH₃ | tert-C₄H₉— | CH=CH₂ | N | m.p. 85° C. |
| 17 | CH₃ | tert-C₄H₉— | CH₂—C₆H₅ | N | m.p. 90–92° C. |
| 18 | CH₃ | tert-C₄H₉— | 4-Cl—C₆H₄—CH₂— | N | m.p. 94–96° C. |
| 19 | n-C₄H₉ | tert-C₄H₉— | CH₃ | N | b.p.(0.01mm)116–120° C. |
| 20 | n-C₄H₉ | tert-C₄H₉— | H | N | b.p.(0.2mm)100–125° C. |
| 21 | CH₃ | 2,4-Cl₂—C₆H₃— | H | CH | oil |
| 22 | C₂H₅ | 2,4-Cl₂—C₆H₃— | H | CH | oil |
| 23 | CH₃ | C₆H₅— | CH₃ | CH | |
| 24 | n-C₄H₉ | 4-Cl—C₆H₄— | CH₃ | CH | |
| 25 | CH₃ | 2,4-Cl₂—C₆H₃— | CH=CH₂ | CH | |
| 26 | CH₃ | 4-(C₆H₅)—C₆H₄— | CH₃ | CH | |
| 27 | CH₃ | 4-Cl—C₆H₄ | CH₃ | CH | oil |
| 28 | C₂H₅ | 2,4-Cl₂—C₆H₃— | 4-Cl—C₆H₄—CH₂— | CH | |
| 29 | CH₃ | tert-C₄H₉— | CH₃ | CH | |
| 30 | CH₃ | tert-C₄H₉— | H | CH | |
| 31 | CH₃ | tert-C₄H₉— | CH=CH₂ | CH | |
| 32 | n-C₄H₉ | tert-C₄H₉— | CH₂—C₆H₅ | CH | |
| 33 | n-C₄H₉ | tert-C₄H₉— | CH₃ | CH | |
| 34 | n-C₄H₉ | tert-C₄H₉— | CH=CH₂ | CH | |
| 35 | CH₃ | 2,4-Cl₂—C₆H₃ | CH₃ | CH | |
| 36 | C₂H₅ | 2,4-Cl₂—C₆H₃ | CH₃ | CH | oil |
| 37 | n-C₃H₇ | 2,4-Cl₂—C₆H₃ | CH₃ | CH | oil |
| 38 | CH₃ | 4-Cl—C₆H₄ | H | CH | |
| 39 | C₂H₅ | 4-Cl—C₆H₄ | H | CH | |

The new compounds may influence practically all the development stages of a plant in different ways; they are therefore used as growth regulators.

The diversity of action of growth regulators depends especially on (a) the type and variety of plant;

(b) the time applied, with reference to the development stage of the plants and the time of year;

(c) the place and method of application (seed treatment, soil treatment, or application to leaves);

(d) geoclimatic factors (sunshine duration, average temperature, precipitate);

(e) soil conditions (including fertilization);

(f) the formulation or application form of the active ingredient; and (g) the concentration at which the active ingredient is applied.

A description of some of the various possibilities of using growth regulators in agriculture and horticulture is given below.

A. With the compounds according to the invention, vegetative plant growth can be inhibited to a considerable extent, a fact which is manifested particularly in a reduction in plant height. The treated plants thus have a compact habit; furthermore, the leaf color is darker.

Of advantage in practice is for example the reduction in grass growth on roadsides, canal embarkments and on areas such as parks, sportsgrounds, fruit orchards, lawns and airfields, thus reducing expensive and time-consuming mowing.

A further feature of economic interest is the increase in the rigor of crops which tend to lodge, such as cereals, Indian corn, sunflowers and soybeans. The shortening and strengthening of the stem thus caused reduces or eliminates the danger of lodging under unfavorable weather conditions.

The use of growth regulators is also important for inhibiting plant height and changing the time of ripening in cotton.

It is thus possible for this important crop to be harvested completely mechanically.

Growth regulators may also increase or inhibit lateral branching. This is of interest when it is desired to inhibit, for instance in tobacco plants, the formation of lateral shoots (suckers) in favor of leaf development.

With growth regulators, it is possible for instance in winter rape to considerably increase the resistance to freeze injury. On the one hand, upward growth and the development of a too luxuriant (and thus particularly frost-susceptible) leaf or plant mass are inhibited; on the other, the young rape plants are kept, in spite of favorable growth conditions, in the vegetative development stage before winter frosts begin. The danger of freeze injury is thus eliminated in plants which tend to lose prematurely their inhibition to bloom and pass into the generative phase. In other crops, too, e.g., winter cereals, it is advantageous if the plants are well tillered in the fall as a result of treatment with the compounds according to the invention, but enter winter with not too lush a growth. This is a preventive measure against increased suspectibility to freeze injury and—because of the relatively low leaf or plant mass—attack by various diseases, especially fungus diseases. The inhibition of vegetative growth also makes closer planting possible in numerous crops, which means an increase in yield, based on the area cropped.

B. Better yields both of plant parts and plant materials may be obtained with the active ingredients according to the invention. It is thus for instance possible to induce increased formation of buds, blossom, leaves, fruit, seed grains, roots and tubers, to increase the sugar content of sugar beets, sugarcane and citrus fruit, to raise the protein content of cereals and soybeans, and to stimulate the increased formation of latex in rubber trees.

The compounds according to the invention may raise the yield by influencing plant metabolism or by promoting or inhibiting vegetative and/or generative growth.

C. Finally, it is also possible with growth regulators to shorten or lengthen growth stages and to accelerate or retard the ripening process in plant parts either before or after harvesting.

A factor of economical interest is for example the facilitation of harvesting made possible by a chemical, temporally concentrated loosening (abscission) of the adherence of stalks to the branches of citrus fruit, olive trees, and other kinds of pomes, drupes and indehiscent fruit. The same mechanism, i.e., promotion of the formation of separation layers between fruit or leaf and stem of the plant, is also essential for a readily controllable defoliation of plants.

The action of the compounds according to the invention is superior to that of prior art growth regulators. This action is manifested not only in monocotyledon crops, e.g., cereals such as wheat, barley, rye, oats, rice, Indian corn or grasses, but also particularly in dicotyledons (e.g., sunflowers, tomatoes, groundnuts, grapes, cotton, rape, and, particularly, soybeans) and various ornamentals such as chrysanthemums, poinsettias and hibiscus.

The novel α-azolylglycols may be applied to the crop either by treating the seed, treating the soil, i.e., through the roots, or by spraying the leaves. Because the active ingredients are well tolerated by the crop plants, application rates may vary within a wide range.

When the active ingredients are used to treat seed, active ingredient amounts of from 0.001 to 50 g, preferably from 0.01 to 10 g, per kg of seed are generally required.

When the active ingredients are applied to the soil or foliage, amounts of from 0.1 to 12 kg/ha, preferably from 0.25 to 3 kg/ha, are generally considered to be sufficient.

The compounds of the invention can be applied in conventional formulations, e.g. solutions, emulsions, suspensions, dusts, powders, pastes and granules. The form of application depends entirely on the purpose for which the agents are being used; in should, however, ensure a fine and uniform distribution of the active ingredient. The formulations are prepared in the conventional manner, for example by diluting the active ingredient with solvents and/or carriers, with or without the addition of emulsifiers and dispersants and, where water is used as the diluent, with or without an organic auxiliary solvent. Suitable auxiliaries are, essentially, solvents, for example aromatics, e.g., xylene and benzene, chloroaromatics, e.g. chlorobenzene, paraffin, e.g. petroleum fractions, alchols, e.g. methanol and butanol, amines, e.g. ethanolamine, and dimethylformamide and water; carriers, for example natural rock powders, e.g. kaolin, alumina, talc and chalk, and synthetic rock powders, e.g. highly disperse silica and silicates; emulsifiers and other surfactants, for example non-ionic and anionic emulsifiers, e.g. polyoxyethylene fatty alcohol ethers, alkylsulfonates and arylsulfonates, and dispersants, for example lignin, sulfite waste liquors and methylcellulose.

The formulations generally contain from 0.1 to 95, and preferably from 0.5 to 90, wt% of active ingredient.

The formulations, and the ready-to-use preparations obtained therefrom, e.g. solutions, emulsions, suspensions, powders, dusts, pastes or granules, are applied in the conventional manner, e.g. preemergence, postemergence, or as seed disinfectants.

Examples A to I illustrate the preparation of formulations.

EXAMPLE A 90 parts by weight of compound 1 is mixed with 10 parts by weight of N-methyl-α-pyrrolidone. A mixture is obtained which is suitable for application in the form of very fine drops.

EXAMPLE B 20 parts by weight of compound 2 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE C 20 parts by weight of compound 3 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

EXAMPLE D 20 parts by weight of compound 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

EXAMPLE E 20 parts by weight of compound 3 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

EXAMPLE F 3 parts by weight of compound 3 is intimately mixed with 97 parts by weight of particulate kaolin. A dust is obtained containing 3% by weight of the active ingredient.

EXAMPLE G 30 parts by weight of compound 4 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE H 40 parts by weight of compound 1 is intimately mixed with 10 parts of the sodium salt of a phenolsulfonic acid-urea-formaldehyde condensate, 2 parts of silica gel and 48 parts of water. Dilution in 100,000 parts by weight of water gives an aqueous dispersion containing 0.04 wt% of active ingredient.

EXAMPLE I 20 parts of compound 2 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The agents according to the invention may, in these application forms, also be mixed and applied with water active ingredients, e.g., herbicides, insecticides, other growth regulators, fungicides and fertilizers. When mixed with other growth regulators, the spectrum of action is in many cases increased; with a number of these compositions, synergistic effects also occur; i.e., the action of the combination product is greater than the effect of the individual components added together.

The action of the compounds to be used in accordance with the invention as plant growth regulators is determined for instance as follows.

To ascertain the growth-regulating properties of the candidate compounds, test plants (spring barley, "Union" variety, and spring rape, "Petronova" variety) were grown in soil provided with sufficient nutrients, in plastic vessels approx. 12.5 cm in diameter.

The candidate compounds were sprayed onto the plants as aqueous formulations. The growth-regulating action observed was confirmed at the end of the experiment by height measurements. The figures obtained were compared with the growth height of untreated plants. The compounds used for comparison purposes were 2-chloroethyl-trimethylammonium chloride and 1-(4'-bromophenyl)-1-allyloxy-2-(1",2",4"-triazol-1"-yl)-ethane.

In these experiments, particularly the compounds of Examples 2, 4, 5, 11, 17 and 19 had an action significantly better than that of the comparative compounds.

Not only was growth height reduced—the leaves also took on a more intense color. The increased chlorophyll content is indicative of a higher rate of photosynthesis, making for bigger yields.

We claim:

1. A process for reducing plant height and/or lateral plant branching which comprises: applying to the plants to be acted upon or to their seeds or to their habitat an effective amount of a composition comprising a liquid or solid carrier and a compound I of the formula

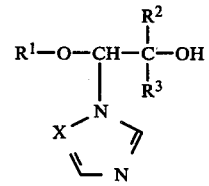

where $R^1$ is alkyl of 1 to 4 carbon atoms, $R^2$ is alkyl of 1 to 6 carbon atoms or unsubstituted or halogen substituted phenyl or biphenyl, $R^3$ is hydrogen, alkyl of 1 to 6 carbon atoms or alkenyl or alkynyl of 2 to 6 carbon atoms or unsubstituted or halogen substituted benzyl and X is CH or N, and their plant-tolerated salts.

* * * * *